(12) United States Patent
Chen

(10) Patent No.: US 7,122,621 B2
(45) Date of Patent: Oct. 17, 2006

(54) ANTI-CELLULAR PROLIFERATIVE DISORDER POLYPEPTIDE

(75) Inventor: Hueih Min Chen, Taipei County (TW)

(73) Assignee: Academia Sinica, Taipei (TW)

( * ) Notice: Subject to any disclaimer, the term of this patent is extended or adjusted under 35 U.S.C. 154(b) by 114 days.

(21) Appl. No.: 10/463,998

(22) Filed: Jun. 17, 2003

(65) Prior Publication Data

US 2004/0259195 A1 Dec. 23, 2004

(51) Int. Cl.
*A61K 38/00* (2006.01)
(52) U.S. Cl. ............... 530/300; 514/12; 424/185.1
(58) Field of Classification Search ............ 514/12; 530/300; 424/12
See application file for complete search history.

(56) References Cited

U.S. PATENT DOCUMENTS 6,153,730 A * 11/2000 Little, II ............... 530/324

FOREIGN PATENT DOCUMENTS

WO    WO 90/12866    * 11/1990

OTHER PUBLICATIONS

Web Printout of secondary structure prediction-4 Pages.*
Boman et al. FEBS Lett 259(1): 103-106 (1989). "Antibacterial and antimalarial properties of peptides that are cecropin-melittin hybrids".*
NCBI AAA26598 Amino acid sequence printout, and Web Printout of secondary structure prediction-2 Pages.*
NCBI AAA29184 Amino acid sequence printout, and Web Printout of secondary structure prediction-2 Pages.*
Siu-Chiu Chan et al. "Enhancement of the Cytolytic Effect of Anti-Bacterial Cecropin by the Microvilli of Cancer Cells". Anti-cancer Research 18:4467-4474, 1998.
Siu-Chiu Chan et al. "Microscopic Observations of the Different Morphological Changes Caused by Anti-bacterial Peptides on *Klebsiella Pneumoniae* and HL-60 Leukemia Cells". Journal of Peptide Science 4:413-425, 1998.
H. M. Chen et al. "Kinetics of membrane lysis by custom lytic peptides and peptide orientations in membrane". Eur. J. Biochem. 268:1659-1669, 2001.
H. M. Chen et al. "Liposome Disruption Detected by Surface Plasma Resonance at Lower Concentrations of a Peptide Antibiotic". Langmuir 16(26):9959-9962, 2000.
Hueih Min Chen et al. "Structure Stability of Lytic Peptides During Their Interactions With Lipid Bilayers". Journal of Biomolecular Structure & Dynamics 19(2):193-199, 2001.
Shao-Ching Hung et al. "Membrane Lysis by the Antibacterial Peptides Cecropins B1 and B3: A Spin-Label Electron Spin Resonance Study on Phospholipid Bilayers". Biophysical Journal 77:3120-3133, Dec. 1999.
S. Srisailam et al. "Conformational study of a customer antibacterial peptide cecropin B1: implications of the lytic activity". Biochimica et Biophysica Acta 1479:275-285, 2000.
S. Srisailam et al. "Crumpled structure of the custom hydrophobic lytic peptide cecropin B3". Eur. J. Biochem. 268:4278-4284, 2001.
Wei Wang et al. "The Dependence of Membrane Permeability by the Antibacterial Peptide Cecropin B and Its Analogs, CB-1 and CB-3, on Liposomes of Different Composition". Journal of Biological Chemistry 273(42):27438-27448, 1998.
Wei Wang et al. The effect of pH on the structure, binding and model membrane lysis by cecropin B and analogs. Biochimica et Biophysica Acta 1473:418-430, 1999.

* cited by examiner

*Primary Examiner*—Jon Weber
*Assistant Examiner*—Anand Desai
(74) *Attorney, Agent, or Firm*—Fish & Richardson P.C.

(57) ABSTRACT

Disclosed is a cell lytic polypeptide that has a region capable of forming an amphipathic alpha helix and a net charge of +12 or more, or that contains 3 regions, each capable of forming an amphipathic alpha helix. A nucleic acid encoding the polypeptide is also disclosed. Also within the scope of this invention are a pharmaceutical composition containing the polypeptide or nucleic acid and a pharmaceutically acceptable carrier, and a method for treating a cellular proliferative disorder.

39 Claims, No Drawings

ANTI-CELLULAR PROLIFERATIVE DISORDER POLYPEPTIDE

BACKGROUND

A cellular proliferative disorder, such as cancer, can be treated by surgery, radiation, and chemotherapy. Among them, chemotherapy is indispensable for inoperable or metastatic forms of cancer. Since most chemotherapeutic agents damage both diseased cells and normal cells, their side effects are severe. Thus, there is a need for chemotherapeutic agents that have little side effects.

SUMMARY

This invention features a polypeptide having cell lysis activity. It can be used to treat a cellular proliferative disorder without severely damaging normal cells. In one example, the polypeptide has a net charge of +12 or more, and contains a region capable of forming an amphipathic alpha helix. Such a helix is a protein motif in which hydrophobic amino acid residues are located predominantly on one side of the helix, and hydrophilic amino acid residues are located predominantly on the opposite side. The region can contain the sequence KWKVFKKIEK (SEQ ID NO: 2).

In another example, the polypeptide of this invention contains 3 regions, each capable of forming an amphipathic alpha helix. Two of the 3 regions can be joined via the linker AGP (SEQ ID NO: 3). The positive charge and negative charge in each region can be +5 and −1, respectively. The amino acid residue at position 2 in each region can be a tryptophan. For example, at least one of the regions contains the sequence SEQ ID NO: 2 shown above. Preferably, all 3 regions of the polypeptide have the same sequence. In one example, the polypeptide contains the sequence of KWKVFKKIEK KWKVFKKIEK AGP KWKVFKKIEK (SEQ ID NO: 1).

The polypeptide of this invention possesses cell lysis activity. Unexpectedly, this activity is more potent against cancer cells than against normal cells. One therefore can use the polypeptide for treating a cellular proliferative disorder, including cancer (e.g., leukemia or stomach carcinoma). Thus, also within the scope of this invention are a pharmaceutical composition that contains the above-described polypeptide and a pharmaceutically acceptable carrier, and a method for treating a cellular proliferative disorder in a subject, i.e., administering to the subject an effective amount of the just-mentioned polypeptide.

This invention also features a nucleic acid containing a sequence encoding the above-described polypeptide. If the nucleic acid is operably linked to a regulatory sequence suitable for expressing the polypeptide in host cells, it can express the polypeptide after being introduced into the host cells. As polypeptides thus-expressed can kill host cells, including cancerous host cells, the nucleic acid can also be used for treating a cellular proliferative disorder in a subject.

The details of one or more embodiments of the invention are set forth in the accompanying description below. Other advantages, features, and objects of the invention will be apparent from the detailed description and the claims.

DETAILED DESCRIPTION

This invention is based, at least in part, on the unexpected discovery of a novel non-naturally occurring polypeptide that has more potent lysis activity against cancer cells than against normal cells. The polypeptide's $IC_{50}$ against cancer cells is less than 20 µM, while its $IC_{50}$ against normal cells is greater than 50 µM, as determined by the assay described in the Example below.

The polypeptide of this invention is highly cationic. Its total net charge is at least +12. The net charge of a polypeptide can be determined by first determining the numbers of acidic amino acid residue (i.e., aspartic acid or glutamic acid) and basic amino acid residues (i.e., lysine, arginine, and histidine) in the polypeptide. The charges for each acidic amino acid residue and basic amino acid residue are counted as −1 and +1, respectively; the charge for each of the other resides is counted as 0. The algebra sum of the charges of all amino acid residues is the total net charge of the polypeptide. One can determine the acidity/basicity of an amino acid residue based on principals well known in the art. See, e.g., Chapter 5, pp 133–161, Biochemistry (3rd Edition) by Christopher K. Mathews, K. E. Van Holde, and Kevin G. Ahern. Benjamin/Cummings, February 2000. This polypeptide has at least one region capable of forming an amphipathic alpha helix, e.g., SEQ ID NO: 2, preferably, the region being 8–12 amino acid resides in length. In one example, the polypeptide has 3 repeats of such regions. In the amphipathic alpha helix, hydrophobic amino acid residues are located predominantly on one side of the helix, and hydrophilic amino acid residues are located predominantly on the opposite side. One can determine the hydrophilicity/hydrophobicity of an amino acid residue in the polypeptide also based on principals well known in the art. See, e.g., Chapter 5, pp 133–161, Biochemistry (3rd Edition) by Christopher K. Mathews, K. E. Van Holde, and Kevin G. Ahern. Benjamin/Cummings, February 2000.

As the polypeptide of this invention is highly cationic, it can easily attach to cell membrane, which is negatively charged. Further, since one side of each the alpha helix of the polypeptide is hydrophobic, it tends to seek an anhydrous environment, such as the region between the two lipid layers of cell membrane. Thus, after the polypeptide attaches to cell membrane, it inserts into the membrane. There, a plurality of the polypeptides aggregate in the membrane, and form pores, eventually leading to cell lysis. See, e.g., Chen H. et al., Eur J Biochem. March;268(6):1659–69, 2001.

The polypeptide of this invention can be synthesized using the method described in the Example below or analogous methods known in the art. It can also be prepared using recombinant technology. For example, one can clone a nucleic acid encoding the polypeptide in an expression vector, in which the nucleic acid is operably linked to a regulatory sequence suitable for expressing the polypeptide in a host cell. One can then introduce the vector into a suitable host cell to express the polypeptide. The expressed recombinant polypeptide can be purified from the host cell by methods such as ammonium sulfate precipitation and fractionation column chromatography. See Goeddel, (1990) Gene Expression Technology: Methods in Enzymology 185, Academic Press, San Diego, Calif. Suitable host cells are those that are resistant to this cell lytic polypeptide. They can be obtained using screening methods known in the art.

A polypeptide thus prepared can be tested for its lysis activity against cancer cells and normal cells according to the method described in the Example below. The polypeptide having higher lysis activity against cancer cells than normal cells can be used for treating a cellular proliferative disorder. A cellular proliferative disorder refers to a disorder characterized by uncontrolled, autonomous cell growth, including malignant and non-malignant growth. An expression vector encoding this polypeptide can also be used for treating this disorder.

To treat a subject having a proliferative disorder, one can administer to a subject in need thereof an effective amount of a pharmaceutical composition that contains the above-descried polypeptide or expression vector and a pharmaceutically acceptable carrier. The term "treating" is defined as administration of a composition to a subject, who has an a cellular proliferative disorder, with the purpose to cure, alleviate, relieve, remedy, prevent, or ameliorate the disorder, the symptom of the disorder, the disease state secondary to the disorder, or the predisposition toward the disorder. An "effective amount" is an amount of the composition that is capable of producing a medically desirable result, e.g., as described above, in a treated subject. The above-described polypeptide can be formulated into dosage forms for different administration routes utilizing conventional methods. For example, the pharmaceutical composition can be administered directly to a proliferation site. The dosage required depends on the choice of the route of administration; the nature of the formulation; the nature of the subject's illness; the subject's size, weight, surface area, age, and sex; and other drugs, if any, being administered. The efficacy of the pharmaceutical composition can be preliminarily evaluated in vitro. For in vivo studies, the composition can be injected into an animal and its effects on a cellular proliferative disorder are then accessed.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE

A polypeptide with the sequence of SEQ ID NO: 1 was synthesized using an Applied Biosystem (ABI) 431 A Peptide Synthesizer as described in Chen H. et al., Biochim. Biophys. Acta 1336:171–179, 1997 and Wang W. et al., J. Biol. Chem. 273:27438–27448, 1998. Briefly, Fmoc chemistry was applied with HBTU/HOBT coupling (ABI Fastmoc 0.25 chemistry cycles). The synthesized polypeptide was deprotected and cleaved from resin using a trifluoroacetic acid solution containing water, phenol, thioanisole and ethanedithiol. The resin was then removed by filtration, and the polypeptide was precipitated with diethyl ether. The precipitate was desalted on Sephadex G-10 (20% acetic acid) and purified using reverse phase HPLC (Vydac C-18 colum, 0.1% TFA in $H_2O$-acetonitrile). The concentration of polypeptide thus-prepared was determined using a bicinchoninic acid assay MICRO BCA PROTEIN ASSAY™; Pierce Chemical Co.). The purity of the polypeptide was determined by analytical HPLC (Vydac C-18, TFA/$H_2O$/acetonitrile) to be greater than 95%. The molecular weight and amino acid composition of the polypeptide were determined by mass spectrometry. The theoretical mass and measured mass were 4190.3 and 4190.0, respectively. The purified polypeptide was lyophilized and weighed on a SARTORIUS RESEARCH MODEL R200D MICROBALANCE™.

The polypeptide thus-prepared, named CHM1, contained 3 repeats of the region having the sequence of SEQ ID NO: 2 and had a total net charge of +12. Each region had a positive charge of +5 and a negative charge of −1.

To evaluate the cell lysis activity of CHM1, a cytotoxcity assay was conducted according to the method described in Chen H. et al., Biochim. Biophys. Acta 1336:171–179, 1997 and Wang W. et al., J. Biol. Chem. 273:27438–27448, 1998.

Anchorage-independent normal cells such as red blood cells and lymphoblast RPMI 7666 cells, and leukemia cell lines such as CCRF-CEM, HL-60, and Jurkat, K-562 cells were respectively maintained in RMPI-1640 culture media containing 10% FBS, 100 unit/ml penicillin G, and 100 µg/ml streptomycin. Cells of each type were seeded at $1 \times 10^5$/ml into a 25 $cm^2$ flask (Falcon) and cultured at 37° C. in the presence of 5% $CO_2$ for two days. The cells were then centrifuged at 1000 rpm for 5 min. The resultant pellet was washed twice with the just-mentioned culture medium, resuspended in an RMPI-1640 medium containing 0.5% FBS, and cultured overnight.

Anchorage-dependent cells such as tissue cells (3T3 cells) or stomach carcinoma (AGS) cells were seeded at $1 \times 10^4$ cells/ml into a 25-$cm^2$ flask containing D-MEM medium supplemented with 10% FBS, 100 unit/ml penicillin G, and 100 µg/ml streptomycin. Cells were grown to about 80% confluence before being trypsinized. The trypsinized cells were resuspended in a D-MEM medium containing 0.5% FBS.

Each of the above-prepared cell suspensions was adjusted so that it contained $1 \times 10^5$ cells/ml before being transferred into 9 wells of a 96-well plate (90 µl/well). The suspension in each well was mixed with 10 ul of a culture medium containing CHM1 freshly prepared from a 500 µM stock solution so that the final concentrations in the 9 wells were 0, 1, 5, 10, 15, 20, 30, 50, and 100 µM, respectively. Triplicates for each well were set up. After incubating for 24 hours, a microtetrazolium (MTT)-based colorimetric assay was conducted. It is known that MTT can be metabolized by mitochondrial dehydrogenases in metabolically active cells to form a formazan salt, which has a strong absorption at 570 nm. To conduct the assay, 20 µl of a solution containing 5 mg/ml MTT (Boehringer Mannheim) was added to each of the wells mentioned above and a well containing 100 µl of PBS. The latter was used as a blank control. After incubating for 4 hours, 100 µl of a solution containing 10% SDS and 0.01 mol/ml HCl was added to each well. The plate was then incubated at 37° C. overnight. The absorbance at 570 nm of the mixture in each well was measured using a Bio-Rad model 450 microtiter plate reader. An average cell survival rate of each triplicate was determined based on the corresponding $\Delta A_{570nm}$ relative to that of the well containing 0 µM CHM1. The survival rates thus obtained were plotted against corresponding CHM1 concentrations to form a cell survival curve and derive the $IC_{50}$. Using the same procedure, also determined were the $IC_{50}$s of other lytic polypeptides, such as cecropin B (CB), cecropin B1 (CB1), Melittin, and Magainin II, and cancer chemotherapeutic agents, such as doxorubicin (DOX), vincristine (VCR), methotrexate (MTX), 5-fluorouracil (5-Fu), cytarabine (Ara-C), 6-mercaptopurine (6-MP). At least three independent experiments were conducted for each of the polypeptides and agents. The results were summarized in Tables 1 and 2 below.

TABLE 1

IC$_{50}$s (µM) of Various Polypeptides and Doxorubicin

| Peptide or Agent | Leukemia cells | | | | Stomach Carcinoma AGS | Normal cells | |
|---|---|---|---|---|---|---|---|
| | CCRF-CEM | HL-60 | Jurkat | K-562 | | Lymphoblast (RPMI7666) | Tissue cells (3T3) |
| CB | 11.7 ± 1.3 | 18.5 ± 1.7 | 31.5 ± 3.0 | >50 | >50 | >200 | >50 |
| CB1 | 4.7 ± 0.2 | 8.1 ± 0.9 | 4.0 ± 0.4 | 15.6 ± 1.8 | 7.1 ± 1.3 | >200 | >50 |
| CHM1 | 4.4 ± 0.3 | 6.7 ± 1.1 | 10.1 ± 1.2 | 8.5 ± 0.6 | 5.6 ± 0.5 | >100 | >50 |
| Melittin | 0.5 ± 0.02 | 0.8 ± 0.02 | 2.5 ± 0.1 | 3.2 ± 0.3 | 0.6 ± 0.02 | NA | 6 ± 0.03 |
| Magainin II | 32.9 ± 0.9 | 38.3 ± 3.2 | 44.0 ± 2.4 | >50 | 28.7 ± 5.0 | NA | >50 |
| Doxorubicin | 0.4 ± 0.1 | 0.19 ± 0.01 | 0.4 ± 0.1 | >10 | 4.1 ± 0.4 | 1.9 ± 0.1 | 2.0 ± 0.7 |

\* NA indicates "Not Available."

TABLE 2

IC$_{50}$s (µM) of Anticancer Chemotherapeutic Agents

| Chemotherapeutic Agents | Cancer Cells | | Lymphoblasts |
|---|---|---|---|
| | CCRF-SB | HL-60 | RPMI 7666 |
| DOX | 0.46 ± 0.07 | 0.19 ± 0.01 | 1.86 ± 0.10 |
| VCR | 0.015 ± 0.01 | 0.034 ± 0.01 | 0.021 ± 0.07 |
| MTX | 0.017 ± 0.01 | 0.018 ± 0.01 | 0.132 ± 0.04 |
| 5-FU | 123.0 ± 30.7 | 7.6 ± 10.5 | 1.15 ± 0.40 |
| Ara-C | 0.10 ± 0.01 | 0.08 ± 0.02 | 0.30 ± 0.10 |
| 6-MP | 0.44 ± 0.01 | 0.43 ± 0.05 | 1.24 ± 0.30 |

As shown in Table 1, CHM1 had higher lysis activity (i.e., a lower IC$_{50}$) than CB and Magainin II against Leukemia cells and stomach carcinoma cells. Although it had lower activity than melittin and most of the chemotherapeutic agents listed in Table 2, it had little effect on normal lymphoblasts and tissue cells.

Effects of CHM1, melittin, CB, CB1 and doxorubicin on red blood cells (RBCs) were also examined. It was found that CHM1 caused much less hemolysis than melittin, CB, CB1, and doxorubicin. In fact, about 15% of RBCs lysed after being treated with CHM1 (200 µM). In contrast, about 100%, 57%, 55%, and 20% of RBCs lysed after being treated by melittin, CB, CB1, and doxorubicin, respectively, at the same concentration.

The above results indicated that CHM1 had cell lysis activity that was more potent against cancer cells than against normal cells.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A purified polypeptide comprising three regions, each capable of forming an amphipathic alpha helix, wherein the polypeptide has cell lysis activity and two of the three regions form two discontinuous amphipathic alpha helixes and wherein each of the regions has the same sequence.

2. The polypeptide of claim 1, wherein the amino acid residue at position 2 in each region is a tryptophan, and the sum of the positive charges and negative charges in each region are +5 and −1, respectively.

3. The polypeptide of claim 2, wherein each region comprises the sequence of SEQ ID NO: 2.

4. The polypeptide of claim 3, wherein two of the regions are joined via a linker having the sequence of SEQ ID NO: 3.

5. The polypeptide of claim 4, comprising the sequence of SEQ ID NO: 1.

6. The polypeptide of claim 1, wherein two of the regions are joined via a linker having the sequence of SEQ ID NO: 3.

7. A method for treating a cellular proliferative disorder in a subject, the method comprising administering to a subject in need thereof an effective amount of the polypeptide of claim 1.

8. The method of claim 7, wherein the cellular proliferative disorder is a cancer.

9. The method of claim 8, wherein the cancer is leukemia or stomach carcinoma.

10. A pharmaceutical composition comprising the polypeptide of claim 1, and a pharmaceutically acceptable carrier.

11. A nucleic acid comprising a sequence encoding the polypeptide of claim 1.

12. A purified polypeptide comprising three regions, each capable of forming an amphipathic alpha helix, wherein the polypeptide has cell lysis activity and two of the three regions form two discontinuous amphipathic alpha helixes and wherein the amino acid residue at position 2 in each region is a tryptophan, and the sum of the positive charges and negative charges in each region are +5 and 1, respectively.

13. The polypeptide of claim 12, wherein at least one of the regions comprises the sequence of SEQ ID NO: 2.

14. The polypeptide of claim 13, wherein two of the regions are joined via a linker having the sequence of SEQ ID NO: 3.

15. The polypeptide of claim 12, wherein two of the regions are joined via a linker having the sequence of SEQ ID NO: 3.

16. A pharmaceutical composition comprising the polypeptide of claim 12 and a pharmaceutically acceptable carrier.

17. A method for treating a cellular proliferative disorder in a subject, the method comprising administering to a subject in need thereof an effective amount of the polypeptide of claim 12.

18. The method of claim 17, wherein the cellular proliferative disorder is a cancer.

19. The method of claim 18, wherein the cancer is leukemia or stomach carcinoma.

20. A nucleic acid comprising a sequence encoding the polypeptide of claim 12.

21. A purified polypeptide comprising three regions, each capable of forming an amphipathic alpha helix, wherein the polypeptide has cell lysis activity and two of the three regions form two discontinuous amphipathic alpha helixes and wherein at least one of the regions comprises the sequence of SEQ ID NO: 2.

22. The polypeptide of claim 21, wherein two of the regions are joined via a linker having the sequence of SEQ ID NO: 3.

23. A pharmaceutical composition comprising the polypeptide of claim 21 and a pharmaceutically acceptable carrier.

24. A method for treating a cellular proliferative disorder in a subject, the method comprising administering to a subject in need thereof an effective amount of the polypeptide of claim 21.

25. The method of claim 24, wherein the cellular proliferative disorder is a cancer.

26. The method of claim 25, wherein the cancer is leukemia or stomach carcinoma.

27. A nucleic acid comprising a sequence encoding the polypeptide of claim 21.

28. A purified polypeptide comprising three regions, each capable of forming an amphipathic alpha helix, wherein the polypeptide has cell lysis activity and two of the three regions form two discontinuous amphipathic alpha helixes and wherein two of the regions are joined via a linker having the sequence of SEQ ID NO: 3.

29. A pharmaceutical composition comprising the polypeptide of claim 28 and a pharmaceutically acceptable carrier.

30. A method for treating a cellular proliferative disorder in a subject, the method comprising administering to a subject in need thereof an effective amount of the polypeptide of claim 28.

31. The method of claim 30, wherein the cellular proliferative disorder is a cancer.

32. The method of claim 31, wherein the cancer is leukemia or stomach carcinoma.

33. A nucleic acid comprising a sequence encoding the polypeptide of claim 28.

34. A purified polypeptide comprising a region capable of forming an amphipathic alpha helix, wherein the polypeptide has a net charge of +12 or more, and possess cell lysis activity, wherein the amino acid residue at position 2 on the region is a tryptophan and wherein the region comprises the sequence of SEQ ID NO: 2.

35. A method for treating a cellular proliferative disorder in a subject, the method comprises administering to a subject in need thereof an effective amount of the polypeptide of claim 34.

36. The method of claim 35, wherein the cellular proliferative disorder is a cancer.

37. The method of claim 36, wherein the cancer is leukemia or stomach carcinoma.

38. A nucleic acid comprising a sequence encoding the polypeptide of claim 34.

39. A pharmaceutical composition comprising the polypeptide of claim 34 and a pharmaceutically acceptable carrier.

* * * * *

SEQUENCE LISTING

```
<160> NUMBER OF SEQ ID NOS: 3

<210> SEQ ID NO 1
<211> LENGTH: 33
<212> TYPE: PRT
<213> ORGANISM: Artificial Sequence
<220> FEATURE:
<223> OTHER INFORMATION: Synthetically generated peptide

<400> SEQUENCE: 1

Lys Trp Lys Val Phe Lys Lys Ile Glu Lys Lys Trp Lys Val Phe Lys
 1               5                  10                  15

Lys Ile Glu Lys Ala Gly Pro Lys Trp Lys Val Phe Lys Lys Ile Glu
            20                  25                  30

Lys

<210> SEQ ID NO 2
<211> LENGTH: 10
<212> TYPE: PRT
<213> ORGANISM: Artificial Sequence
<220> FEATURE:
```

-continued

```
<223> OTHER INFORMATION: Synthetically generated peptide

<400> SEQUENCE: 2

Lys Trp Lys Val Phe Lys Lys Ile Glu Lys
1               5                   10

<210> SEQ ID NO 3
<211> LENGTH: 36
<212> TYPE: PRT
<213> ORGANISM: Artificial Sequence
<220> FEATURE:
<223> OTHER INFORMATION: Synthetically generated peptide

<400> SEQUENCE: 3

Lys Trp Lys Val Phe Lys Lys Ile Glu Lys Ala Gly Pro Lys Trp Lys
1               5                   10                  15

Val Phe Lys Lys Ile Glu Lys Ala Gly Pro Lys Trp Lys Val Phe Lys
            20                  25                  30

Lys Ile Glu Lys
            35
```